United States Patent
Iwamoto et al.

(10) Patent No.: US 11,691,935 B2
(45) Date of Patent: *Jul. 4, 2023

(54) PRODUCTION METHOD FOR FLUORO-ETHANE AND PRODUCTION METHOD FOR FLUORO-OLEFIN

(71) Applicant: DAIKIN INDUSTRIES, LTD., Osaka (JP)

(72) Inventors: Tomoyuki Iwamoto, Osaka (JP); Takashi Usui, Osaka (JP); Takehiro Chaki, Osaka (JP); Tsubasa Nakaue, Osaka (JP); Kazuhiro Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/350,664

(22) Filed: Jun. 17, 2021

(65) Prior Publication Data

US 2021/0317054 A1    Oct. 14, 2021

Related U.S. Application Data

(63) Continuation of application No. PCT/JP2019/049595, filed on Dec. 18, 2019.

(30) Foreign Application Priority Data

Dec. 19, 2018    (JP) .............................. JP2018-237658

(51) Int. Cl.
| | | |
|---|---|---|
| C07C 17/354 | (2006.01) | |
| C07C 17/23 | (2006.01) | |
| B01J 23/44 | (2006.01) | |
| C07C 17/25 | (2006.01) | |

(52) U.S. Cl.
CPC .............. *C07C 17/23* (2013.01); *B01J 23/44* (2013.01); *C07C 17/25* (2013.01); *C07C 17/354* (2013.01)

(58) Field of Classification Search
CPC .................................................. C07C 17/354
See application file for complete search history.

(56) References Cited

U.S. PATENT DOCUMENTS 3,432,562 A * 3/1969 Gardner .................. C07C 17/25
570/156
5,059,729 A    10/1991 Gervasutti
5,626,790 A * 5/1997 Minor ...................... C08J 9/149
252/67

| 2011/0071325 | A1 | 3/2011 | Ohno et al. |
| 2013/0006022 | A1 | 1/2013 | Shiotani et al. |
| 2016/0168059 | A1 | 6/2016 | Shiotani et al. |
| 2017/0327442 | A1 | 11/2017 | Wendlinger |
| 2019/0169101 | A1 | 6/2019 | Karube et al. |

FOREIGN PATENT DOCUMENTS

| EP | 0 234 002 | 9/1987 |
| EP | 3 792 237 | 3/2021 |
| GB | 2 311 522 | 10/1997 |
| JP | 62-169737 | 7/1987 |
| JP | 1-287044 | 11/1989 |
| JP | 9-255598 | 9/1997 |
| JP | 2010-533151 | 10/2010 |
| JP | 2017-537131 | 12/2017 |
| WO | 2009/010472 | 1/2009 |
| WO | 2009/139352 | 11/2009 |
| WO | 2011/122157 | 10/2011 |
| WO | 2012/094477 | 7/2012 |
| WO | 2016/092340 | 6/2016 |
| WO | 2017/104828 | 6/2017 |
| WO | 2018/012511 | 1/2018 |
| WO | 2019/216175 | 11/2019 |

OTHER PUBLICATIONS

Sigma "Trifluoroethylene" Deposited and Available date Mar. 3, 2017 (Year: 2017).*
International Search Report dated Mar. 10, 2020 in International (PCT) Application No. PCT/JP2019/049595.
International Search Report dated Mar. 10, 2020 in International (PCT) Application No. PCT/JP2019/049608.
International Search Report dated Apr. 14, 2020 in International (PCT) Application No. PCT/JP2020/002548.
Extended European Search Report dated Sep. 2, 2022 in corresponding European Patent Application No. 19898555.8.
Extended European Search Report dated Sep. 2, 2022 in European Patent Application No. 19899310.7.
Extended European Search Report dated Oct. 13, 2022 in European Patent Application No. 20746006.4.

* cited by examiner

*Primary Examiner* — Medhanit W Bahta
(74) *Attorney, Agent, or Firm* — Wenderoth, Lind & Ponack, L.L.P.

(57) ABSTRACT

The production method according to the present disclosure comprises obtaining a product containing the fluoroethane from a fluoroethylene by a reaction in the presence of catalysts. Each catalyst is formed by supporting a noble metal on a carrier. A reactor for performing the reaction is filled with a catalyst having a noble metal concentration of C1 mass % based on the entire catalyst and a catalyst having a noble metal concentration of C2 mass % based on the entire catalyst to form an upstream portion and a downstream portion, respectively; and C1<C2. The reaction is performed by bringing the fluoroethylene represented by formula (3) and hydrogen gas into contact with the upstream portion and the downstream portion in this order.

4 Claims, No Drawings

PRODUCTION METHOD FOR FLUORO-ETHANE AND PRODUCTION METHOD FOR FLUORO-OLEFIN

TECHNICAL FIELD

The present disclosure relates to a method for producing a fluoroethane, and a method for producing a fluoroolefin.

BACKGROUND ART

Fluoroethanes typified by 1,1,2-trifluoroethane (hereinafter referred to "HFC-143") are known as a starting material for producing various refrigerants. Various methods have been proposed for the production of fluoroethanes such as HFC-143.

For example, Patent Literature 1 proposes a technique for producing HFC-143 by a hydrogenation reaction of chlorotrifluoroethylene or the like, in the presence of a hydrogenation catalyst.

CITATION LIST

Patent Literature

PTL 1: JPH1-287044A

SUMMARY

Solution to Problem

For example, the present disclosure includes the inventions described in the following items.

Item 1

A method for producing a fluoroethane represented by the following formula (1):

$$CX^1X^2FCX^3X^4X^5 \qquad (1),$$

wherein $X^1$, $X^2$, $X^3$, $X^4$, and $X^5$ are the same or different and each represents a hydrogen atom, a fluorine atom, or a chlorine atom; and at least one of $X^1$, $X^2$, $X^3$, $X^4$, and $X^5$ represents a hydrogen atom,
the method comprising obtaining a product comprising the fluoroethane from a fluoroethylene represented by the following formula (3) by a reaction in the presence of catalysts:

$$CX^9F=CX^{10}X^{11} \qquad (3),$$

wherein $X^9$, $X^{10}$, and $X^{11}$ are the same or different and each represents a hydrogen atom, a fluorine atom, or a chlorine atom,
wherein each catalyst is formed by supporting a noble metal on a carrier;
a reactor for performing the reaction is filled with a catalyst having a noble metal concentration of C1 mass % based on the entire catalyst, and a catalyst having a noble metal concentration of C2 mass % based on the entire catalyst to form an upstream portion and a downstream portion, respectively, and C1<C2; and
the reaction is performed by bringing the fluoroethylene represented by formula (3) and hydrogen gas into contact with the upstream portion and the downstream portion in this order.

Advantageous Effects of Invention

The production method according to the present disclosure enables the desired fluoroethane to be obtained with high selectivity.

DESCRIPTION OF EMBODIMENTS

The present inventors found that in the production of a fluoroethane, when a fluoroethane such as HFC-143 (1,1,2-trifluoroethane) is produced according to, for example, the method disclosed in Patent Literature 1, the selectivity of the desired fluoroethane is poor in many cases.

The inventors also confirmed that the method disclosed in Patent Literature 1 causes significant blockage and corrosion of the reactor during the reaction. In particular, when the capacity of the reactor is increased (i.e., when the reactor is scaled up for mass production), the selectivity decreases more notably, and blockage and corrosion of the reactor occur during the reaction.

The inventors conducted extensive research to achieve an object of providing a production method that enables the desired fluoroethane to be obtained with high selectivity, and that is less likely to cause blockage and corrosion of the reactor. The inventors consequently found that the above object can be achieved by providing a gradient to the amount of noble metal in a catalyst containing a noble metal supported on a carrier.

Embodiments included in the present disclosure are described in detail below. In the present specification, the terms "comprise" and "contain" include the concepts of "comprise," "contain," "consist essentially of," and "consist of."

1. Method for Producing Fluoroethane

In the production method according to the present disclosure, a fluoroethane represented by the following formula (1) is produced:

$$CX^1X^2FCX^3X^4X^5 \qquad (1),$$

wherein $X^1$, $X^2$, $X^3$, $X^4$, and $X^5$ are the same or different and each represents a hydrogen atom, a fluorine atom, or a chlorine atom; and at least one of $X^1$, $X^2$, $X^3$, $X^4$, and $X^5$ represents a hydrogen atom.

The production method according to the present disclosure comprises obtaining a product comprising the fluoroethane from a fluoroethylene represented by the following formula (3) by a reaction in the presence of catalysts:

$$CX^9F=CX^{10}X^{11} \qquad (3),$$

wherein $X^9$, $X^{10}$, and $X^{11}$ are the same or different and each represents a hydrogen atom, a fluorine atom, or a chlorine atom.

Hereinafter, in the present specification, the method for producing a fluoroethane according to the present disclosure is referred to as "Production Method 1 according to the present disclosure."

In particular, in Production Method 1 according to the present disclosure, each catalyst is formed by supporting a noble metal on a carrier. A reactor for performing the hydrogenation reaction is filled with a catalyst having a noble metal concentration of C1 mass % based on the entire catalyst, and a catalyst having a noble metal concentration of C2 mass % based on the entire catalyst to form an upstream portion and a downstream portion, respectively; and C1<C2. The hydrogenation reaction is performed by bringing the fluoroethylene represented by formula (3) and hydrogen gas into contact with the upstream portion and the downstream portion in this order.

In Production Method 1 according to the present disclosure, the desired product is a fluoroethane represented by formula (1) (hereinafter simply referred to as "fluoroethane"). In addition to the fluoroethane, by-products may also be produced in Production Method 1 according to the present disclosure. Thus, the product may be a mixed gas of the desired product and a by-product.

In Production Method 1 according to the present disclosure, examples of by-products include a fluoroethylene represented by the following formula (2):

$$CX^6F=CX^7X^8 \qquad (2)$$

wherein $X^6$, $X^7$, and $X^8$ are the same or different and each represents a hydrogen atom, a fluorine atom, or a chlorine atom; and at least one of $X^6$, $X^7$, and $X^8$ represents a hydrogen atom.

Production Method 1 according to the present disclosure enables the desired fluoroethane to be obtained with high selectivity. Moreover, in Production Method 1 according to the present disclosure, blockage and corrosion of the reactor are less likely to occur during the hydrogenation reaction.

Product

In Production Method 1 according to the present disclosure, the fluoroethane contained in the product is the main product and the desired product in Production Method 1 according to the present disclosure. The term "main product" as used herein means a component that is present in an amount of 50 mol % or more in the product.

The fluoroethane is not limited, as long as it is a compound represented by formula (1). In formula (1), at least one of $X^1$, $X^2$, $X^3$, $X^4$, and $X^5$ represents a hydrogen atom; for example, $X^5$ may be a hydrogen atom. It is preferable that at least one of $X^1$, $X^2$, $X^3$, $X^4$, and $X^5$ is a fluorine atom.

Specific examples of the fluoroethane include at least one member selected from the group consisting of 1-chloro-1-fluoroethane (HCFC-151), fluoroethane (HFC-161), 1,2-dichloro-1,2-difluoroethane (HCFC-132), 2-chloro-1,1-difluoroethane (HCFC-142), 1-chloro-1,2-difluoroethane (HCFC-142a), 1,2-difluoroethane (HFC-152), 1,1-difluoroethane (HFC-152a), 2-chloro-1,1,2-trifluoroethane (HCFC-133), 1-chloro-1,1,2-trifluoroethane (HCFC-133b), 1,1,1-trifluoroethane (HFC-143a), 1,1,2-trifluoroethane (HFC-143), 1,1,2,2-tetrafluoroethane (HFC-134), and 1,1,1,2-tetrafluoroethane (HFC-134a).

In Production Method 1 according to the present disclosure, one or more of the fluoroethanes described above are produced. That is, in Production Method 1, the product comprises one or more of the fluoroethanes described above. It is more preferable that the one or more fluoroethanes, which are the main product in Production Method 1 according to the present disclosure, comprise at least 1,1,2-trifluoroethane (HFC-143); and it is particularly preferable that 1,1,2-trifluoroethane (HFC-143) is the main product. When 1,1,2-trifluoroethane (HFC-143) is the main product, for example, HCFC-133 and HCFC-133b may also be produced simultaneously.

Among by-products that may be produced in Production Method 1 according to the present disclosure, the fluoroethylene represented by formula (2) preferably comprises at least one member selected from the group consisting of trifluoroethylene (HFO-1123), 1,2-difluoroethylene (HFO-1132), 1,1-difluoroethylene (HFO-1132a), fluoroethylene (HFO-1141), 1-chloro-2-fluoroethylene, and 1,2-dichloro-fluoroethylene (HCFO-1121). The fluoroethylene represented by formula (2) particularly preferably comprises trifluoroethylene (HFO-1123) among these. In Production Method 1 according to the present disclosure, one or more by-products are produced.

In Production Method 1, the product preferably comprises 1,1,2-trifluoroethane in an amount of 60 mol % or more, more preferably 70 mol % or more, and particularly preferably 80 mol % or more, based on the total amount of the product.

In Production Method 1, the product preferably comprises trifluoroethylene in an amount of 40 mol % or less, more preferably 30 mol % or less, and particularly preferably 20 mol % or less, based on the total amount of the product.

In Production Method 1, the product may be purified to increase the purity of the desired compound, or the product obtained without purification may be used as the desired compound. Moreover, when the product contains an unreacted starting material, the starting material can be separated by an appropriate method and used again as a starting material for the reaction. Specifically, in Production Method 1, the crude product can be used for recycling a starting material.

Starting Material

In Production Method 1 according to the present disclosure, the fluoroethylene represented by formula (3) is a starting material for obtaining the desired product and a starting material for the reaction performed in Production Method 1 according to the present disclosure. The fluoroethylene represented by formula (3) can be suitably selected according to the structural formula of the desired fluoroethane.

For example, the fluoroethylene represented by formula (3) is preferably at least one member selected from the group consisting of fluoroethylene (HFO-1141), 1,2-dichloro-1,2-difluoroethylene (CFO-1112), 1,1-difluoroethylene (HFO-1132a), 1,2-difluoroethylene (HFO-1132), chlorotrifluoroethylene (CTFE, CFO-1113), trifluoroethylene (HFO-1123), 2-chloro-1,1-difluoroethylene (HCFO-1122), 1-chloro-1,2-difluoroethylene (HCFO-1122a), and tetrafluoroethylene (FO-1114). Among these, the fluoroethylene more preferably comprises at least one member selected from the group consisting of chlorotrifluoroethylene (CTFE, CFO-1113) and tetrafluoroethylene (FO-1114); the fluoroethylene particularly preferably comprises chlorotrifluoroethylene (CTFE, CFO-1113).

The fluoroethylenes represented by formula (3) may be used singly, or in a combination of two or more. When a single fluoroethylene represented by formula (3) is used, the fluoroethylene may contain, for example, impurities that may be inevitably present; or other components.

Catalyst

In Production Method 1 according to the present disclosure, the fluoroethylene represented by formula (3) is subjected to a reaction in the presence of catalysts. As described later, the reaction is, for example, a hydrogenation reaction, and an accompanying dehydrochlorination reaction and hydrogen chloride addition reaction.

In Production Method 1 according to the present disclosure, the type of catalyst is not limited as long as a catalyst formed by supporting a noble metal on a carrier is used. For example, a wide range of known catalysts used in a hydrogenation reaction can be used.

Examples of the noble metal in each catalyst used in Production Method 1 according to the present disclosure include palladium (Pd), platinum (Pt), ruthenium (Ru), rhodium (Rh), nickel (Ni), cobalt (Co), and the like. The noble metal is preferably one or more members selected from the group consisting of palladium, platinum, and nickel. The noble metal particularly preferably comprises palladium.

Examples of the carrier in each catalyst used in Production Method 1 according to the present disclosure include activated carbon, porous aluminosilicate typified by zeolite, aluminum oxide, silicon oxide, titanium oxide, zirconium oxide, zinc oxide, aluminum fluoride, and the like. The carrier may be formed of only one material, or may be formed of two or more materials.

In Production Method 1 according to the present disclosure, in particular, the reactor in which the reaction is performed is filled with a catalyst having a noble metal concentration of C1 mass % based on the total mass of the catalyst, and a catalyst having a noble metal concentration of C2 mass % based on the total mass of the catalyst to form the former as an upstream portion and the latter as a downstream portion. In Production Method 1, C1<C2.

The reaction is performed by forming the catalyst of the upstream portion and the catalyst of the downstream portion in the above manner, and bringing the fluoroethylene represented by formula (3) and hydrogen gas into contact with the upstream portion and the downstream portion in this order. Thus, the upstream portion and the downstream portion in the present disclosure respectively refer to the inlet side into which the fluoroethylene represented by formula (3), which is a starting material, is introduced; and the outlet side.

In Production Method 1 according to the present disclosure, the positions of the upstream portion and the downstream portion provided in the reactor are not limited. For example, the upstream portion and the downstream portion may be provided so as to be adjacent to each other, or the upstream portion and the downstream portion may be provided with a gap between them. Further, a catalyst may be placed between the upstream portion and the downstream portion to form a midstream portion. The midstream portion may be formed of only one layer, or two or more layers. When the noble metal concentration of the catalyst forming the midstream portion is expressed as $C^M$ mass %, the noble metal concentration may be set such that $C1<C^M<C2$.

The thicknesses of the upstream portion and the downstream portion are also not limited; and can be suitably selected depending on, for example, the size of the reactor and the gas flow rate. The thicknesses of the upstream portion and the downstream portion refer to the lengths in the direction in which the starting materials flow.

In the upstream portion, the amount of noble metal supported, i.e., C1 (mass %), based on the total mass of the catalyst may be adjusted, for example, to 0.01 to 10 mass %, and preferably 0.1 to 3 mass %.

In the downstream portion, the amount of noble metal supported, i.e., C2 (mass %), based on the total mass of the catalyst may be adjusted, for example, to 1 to 15 mass %, and preferably 1 to 5 mass %.

The method for preparing the catalyst is not limited, and a wide range of know methods can be used. An example of the method for preparing a catalyst comprising a noble metal supported on a carrier is as below. That is, a carrier is immersed in a solution containing a noble metal to impregnate the carrier with the solution, if necessary, followed by neutralization, calcination, and the like, thereby obtaining the catalyst. In this case, the amount of noble metal supported on the carrier can be controlled by adjusting the concentration of the solution, the impregnation time, and the like.

In Production Method 1 according to the present disclosure, the amount of catalyst used is not limited; and may be, for example, the same as or similar to that in known hydrogenation reactions. For example, the amount of catalyst used can be suitably set depending on the size of the reactor, the amount of starting material used, the amount of fluoroethane to be produced, and the like.

Reaction

In Production Method 1 according to the present disclosure, the reaction is, for example, a hydrogenation reaction. In Production Method 1 according to the present disclosure, the reaction may also include one or both of a dehydrochlorination reaction and a hydrogen chloride addition reaction, in addition to the hydrogenation reaction.

In Production Method 1 according to the present disclosure, the reaction is performed by reacting the fluoroethylene represented by formula (3) with hydrogen gas in the presence of catalysts in a reactor. This reaction is generally performed in a gas phase. In Production Method 1 according to the present disclosure, the reaction can be performed either continuously, or batch-wise.

Specifically, in Production Method 1 according to the present disclosure, when the fluoroethylene represented by formula (3) and hydrogen gas are introduced into a reactor filled with catalysts to bring the fluoroethylene and hydrogen gas into contact with the catalysts, a hydrogenation reaction proceeds; and further, a dehydrochlorination reaction and hydrogen chloride addition reaction accompanying the hydrogenation reaction can also proceed. The fluoroethylene and hydrogen gas pass through the catalysts while they are brought into contact with the catalyst of the upstream portion and the catalyst of the downstream portion in this order, and flow through the reactor; and a product containing the desired fluoroethane is then collected, for example, as a mixed gas outside the reactor. The mixed gas may also comprise the by-products described above, such as a fluoroethylene represented by formula (2), in addition to the desired fluoroethane.

In Production Method 1 according to the present disclosure, when either one or both of a dehydrochlorination reaction and a hydrogen chloride addition reaction proceed as side reactions during the hydrogenation reaction, by-products, such as a fluoroethylene represented by formula (2), may be produced in addition to the desired fluoroethane.

The reactor may be, for example a tubular flow reactor. For example, the flow reactor may be an adiabatic reactor, a multitubular reactor in which a heating medium is used to slowly cool the reactor, or the like. The reactor is preferably formed of a material that is resistant to corrosive action, such as stainless steel (SUS). In particular, the reactor is preferably formed of Hastelloy, Inconel, Monel, or the like.

The reactor may also be provided with a jacket for adjusting the temperature inside the reactor. For example, a heating medium or the like may be circulated in the jacket. This makes it possible to adjust the temperature of the gases (e.g., starting materials fluoroethylene and hydrogen) in the reactor.

In Production Method 1 according to the present disclosure, the reaction may be performed under reduced pressure, atmospheric pressure, or increased pressure. For example, in Production Method 1 according to the present disclosure, the pressure during the reaction is preferably 2 MPaG or less, more preferably 1 MPaG or less, and particularly preferably 0.3 MPaG or less, from the viewpoint of reactivity. The G in "MPaG" means gauge pressure, and indicates the value displayed on a pressure gauge relative to atmospheric pressure (i.e., atmospheric pressure=0 MPaG). Moreover, the reaction may also be performed either in the presence of an inert gas, or in the presence of air.

In Production Method 1 according to the present disclosure, the reaction temperature in the upstream portion (the ambient temperature when the starting materials come into contact with the upstream portion) may be 100 to 500° C., and preferably 200 to 400° C. In Production Method 1 according to the present disclosure, the reaction temperature in the downstream portion (the ambient temperature when the starting materials come into contact with the downstream portion) can be suitably adjusted depending on the type of desired product. The reaction temperature in the downstream portion may be, for example, 100 to 400° C., and preferably 150 to 300° C. The reaction temperature in the upstream portion is preferably 400° C. or less, from the viewpoint of preventing, for example, polymerization of the fluoroethylene, which is a starting material, explosion, and catalyst deterioration; and the temperature can be adjusted by cooling as necessary.

In Production Method 1 according to the present disclosure, the amount of hydrogen gas used in the reaction is not limited, and may be, for example, the same as or similar to that in known hydrogenation reactions. For example, the amounts of the fluoroethylene represented by formula (3) and hydrogen gas can be adjusted so that the amount of hydrogen gas is 1 to 25 moles, per mole of the fluoroethylene represented by formula (3), which is used a starting material. The amount of hydrogen gas is preferably 1 to 15 moles, and more preferably 1 to 10 moles, per mole of the fluoroethylene represented by formula (3).

In Production Method 1 according to the present disclosure, the reaction time of the hydrogenation reaction is not limited. For example, the contact time represented by W/Fo, i.e., the ratio of the catalyst amount in the reactor W (g) to the total flow rate of the fluoroethylene and hydrogen gas introduced into the reactor Fo, may be 1 to 100 g·sec/cc.

Production Method 1 according to the present disclosure may also comprise, if necessary, other steps in addition to the step of obtaining the fluoroethane.

In Production Method 1 according to the present disclosure, the catalysts filled into the reactor form the upstream portion and the downstream portion. Accordingly, the fluoroethylene represented by formula (3) and hydrogen gas first pass through the catalyst having lower activity, and then pass through the catalyst in the downstream portion that has higher activity than the upstream portion. This makes it easier to suppress a fluoroethylene polymerization reaction, which occurs as a side reaction in conventional methods, resulting in significant suppression of an excessive temperature rise in the reactor and of the amount of polymer of fluoroethylene produced. Moreover, the amount of intermediate product and by-product of the hydrogenation reaction mixed in the ultimately obtained fluoroethane can be notably suppressed. Thus, in Production Method 1 according to the present disclosure, the selectivity and yield of the product can be controlled by the catalyst in the downstream portion and the reaction temperature. Further, a mixture of fluoroethylene and fluoroethane can also be obtained while ensuring high conversion and high selectivity, by adjusting the reaction conditions.

In addition to the problem of poor selectivity of the desired product, conventional methods (e.g., the method disclosed in Patent Literature 1) have the problem of causing blockage and corrosion of the reactor. In contrast, Production Method 1 according to the present disclosure makes it possible to easily suppress a fluoroethylene polymerization reaction, and thus has an advantage such that blockage and corrosion of the reactor due to the formation of a polymer are less likely to occur.

In Production Method 1 according to the present disclosure, for example, when chlorotrifluoroethylene is used as a starting material, the intermediate product of the hydrogenation reaction comprises trifluoroethylene. In Production Method 1 according to the present disclosure, for example, when chlorotrifluoroethylene is used as a starting material, the by-product of the hydrogenation reaction is one or more members selected from 1-chloro-1-fluoroethane (HCFC-151), fluoroethane (HFC-161), chloro-1,2-difluoroethane (HCFC-142), 1,2-difluoroethane (HFC-152), 1,1-difluoroethane (HFC-152a), 2-chloro-1,1,2-trifluoroethane (HCFC-133), 1-chloro-1,1,2-trifluoroethane (HCFC-133b), 1,1,1-trifluoroethane (HFC-143a), trifluoroethylene (HFO-1123), 1,1-difluoroethylene (HFO-1132a), 1,2-difluoroethylene (HFO-1132), ethylene, chloroethane, and the like.

Production Method 1 according to the present disclosure, which allows a fluoroethane to be produced with high selectivity, is particularly useful as a method for producing HFC-143, which is used as a starting material for producing 1,2-difluoroethylene (HFO-1132), a promising post-R32 refrigerant.

2. Method for Producing Fluoroolefin

The method for producing a fluoroolefin according to the present disclosure comprises obtaining a fluoroolefin by a dehydrofluorination reaction of a fluoroethane obtained in the method for producing a fluoroethane described above (Production Method 1). Hereinafter, this step is referred to as "the dehydrofluorination step," and the method for producing a fluoroolefin according to the present disclosure is referred to as "Production Method 2 according to the present disclosure."

In Production Method 2 according to the present disclosure, for example, a fluoroolefin represented by the following formula (4) can be obtained:

$$CX^{11}X^{21}=CX^{31}X^{41} \qquad (4)$$

wherein $X^{11}$, $X^{21}$, $X^{31}$, and $X^{41}$ are the same or different and each represents a hydrogen atom, a fluorine atom, or a chlorine atom; at least one of $X^{11}$, $X^{21}$, $X^{31}$, and $X^{41}$ represents a hydrogen atom; and at least one of $X^{11}$, $X^{21}$, $X^{31}$, and $X^{41}$ represents a fluorine atom.

In the dehydrofluorination step, the method for the dehydrofluorination reaction is not limited. For example, the dehydrofluorination reaction may be performed under conditions that are the same as or similar to those of known dehydrofluorination reactions. For example, the dehydrofluorination reaction may be performed in a gas phase, in the presence of a catalyst for dehydrofluorination.

In Production Method 2 according to the present disclosure, the dehydrofluorination reaction when 1,1,2-trifluoroethane (HFC-143) is used as a fluoroethane is performed according to the following reaction scheme.

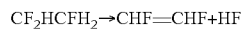

$$CF_2HCFH_2 \rightarrow CHF=CHF+HF$$

The catalyst for dehydrofluorination is not limited, and a wide range of known catalysts can be used. Examples include chromium oxide, fluorinated chromium oxide, aluminum oxide, fluorinated aluminum oxide, and the like.

The catalyst for dehydrofluorination is preferably supported on a carrier. Examples of carriers include carbon, alumina ($Al_2O_3$), zirconia ($ZrO_2$), silica ($SiO_2$), titania ($TiO_2$), and the like. As carbon, activated carbon, amorphous carbon, graphite, diamond, or the like can be used.

In Production Method 2 according to the present disclosure, the dehydrofluorination reaction may also be performed in the presence of an oxidizing agent. Examples of oxidizing agents include oxygen, chlorine, bromine, iodine, and the like. Oxygen is particularly preferable. The concentration of the oxidizing agent is not limited; and may be, for example, the same as or similar to that in known dehydrofluorination reactions.

The reaction temperature in the dehydrofluorination reaction is also not limited; and may be the same as or similar to that in known dehydrofluorination reactions. For example, the reaction temperature in the dehydrofluorination reaction may be, for example, 300° C. or more, preferably 320° C. or more, more preferably 340° C. or more, and particularly preferably 350° C. or more. The reaction temperature in the dehydrofluorination reaction may also be 600° C. or less, preferably 550° C. or less, more preferably 500° C. or less, and particularly preferably 450° C. or less.

The reaction time of the dehydrofluorination reaction and the pressure during the reaction are also not limited, and a wide range of known conditions can be adopted. The dehydrofluorination reaction may also be performed either in the presence of an inert gas, or in the presence of air. The dehydrofluorination reaction may be performed either continuously, or batch-wise.

Production Method 2 according to the present disclosure may also comprise, if necessary, other steps in addition to the dehydrofluorination step. Also in Production Method 2, the starting material can be separated from the crude product obtained in Production Method 2, and recycled.

For example, a compound represented by formula (4) is obtained as the desired fluoroolefin by the dehydrofluorination step. In the dehydrofluorination step, one or more fluoroolefins are produced as the desired compounds.

The resulting fluoroolefin can depend on the fluoroethane used in the dehydrofluorination step. Examples of fluoroolefins include 1,2-difluoroethylene (HFO-1132), 1,1-difluoroethylene (HFO-1132a), trifluoroethylene (HFO-1123), and the like.

In Production Method 2 according to the present disclosure, when HFC-143 is used as a fluoroethane, the resulting fluoroolefin is HFO-1132. In Production Method 2 according to the present disclosure, when HFC-143a is used as a fluoroethane, the resulting fluoroolefin is HFO-1132a. In Production Method 2 according to the present disclosure, when HFC-134 is used as a fluoroethane, the resulting fluoroolefin is HFO-1123. HFO-1132 can include trans-1,2-difluoroethylene [(E)-HFO-1132] and cis-1,2-difluoroethylene [(Z)-HFO-1132].

When a fluoroolefin is obtained by Production Method 2 according to the present disclosure, Production Method 1 according to the present disclosure and Production Method 2 according to the present disclosure may be performed consecutively, or may be performed independently.

For example, the present disclosure includes the inventions described in the following items.

Item 1

A method for producing a fluoroethane represented by the following formula (1):

$$CX^1X^2FCX^3X^4X^5 \quad (1),$$

wherein $X^1$, $X^2$, $X^3$, $X^4$, and $X^5$ are the same or different and each represents a hydrogen atom, a fluorine atom, or a chlorine atom; and at least one of $X^1$, $X^2$, $X^3$, $X^4$, and $X^5$ represents a hydrogen atom, the method comprising obtaining a product comprising the fluoroethane from a fluoroethylene represented by the following formula (3) by a reaction in the presence of catalysts:

$$CX^9F=CX^{10}X^{11} \quad (3),$$

wherein $X^9$, $X^{10}$, and $X^{11}$ are the same or different and each represents a hydrogen atom, a fluorine atom, or a chlorine atom, wherein each catalyst is formed by supporting a noble metal on a carrier;

a reactor for performing the reaction is filled with a catalyst having a noble metal concentration of C1 mass % based on the entire catalyst, and a catalyst having a noble metal concentration of C2 mass % based on the entire catalyst to form an upstream portion and a downstream portion, respectively, and C1<C2; and the reaction is performed by bringing the fluoroethylene represented by formula (3) and hydrogen gas into contact with the upstream portion and the downstream portion in this order.

Item 2

The method for producing a fluoroethane according to Item 1, wherein the noble metal is palladium.

Item 3

The method for producing a fluoroethane according to Item 1 or 2, wherein the fluoroethylene represented by formula (3) comprises chlorotrifluoroethylene.

Item 4

The method for producing a fluoroethane according to any one of Items 1 to 3, wherein the fluoroethane comprises 1,1,2-trifluoroethane.

Item 5

The method according to Item 4, wherein the product comprises 1,1,2-trifluoroethane in an amount of 60 mol % or more based on the total amount of the product.

Item 6

The method according to any one of Items 1 to 5, wherein the product comprises trifluoroethylene in an amount of 40 mol % or less based on the total amount of the product.

Item 7

A method for producing a fluoroolefin, the method comprising obtaining a fluoroolefin by a dehydrofluorination reaction of a fluoroethane obtained by the method according to any one of Items 1 to 6.

EXAMPLES

The present disclosure is described in more detail below with reference to Examples. However, the present disclosure is not limited to the Examples.

Example 1

One 50 A reaction tube was prepared and filled with 670 g of catalysts. Each catalyst was formed using activated carbon as a carrier, and using palladium as a noble metal. When the reaction tube was filled with the catalysts, a catalyst containing palladium in an amount of 0.3 mass % based on the total mass of the catalyst was formed as an upstream portion, and a catalyst containing palladium in an amount of 3 mass % based on the total mass of the catalyst was formed as a downstream portion. Chlorotrifluoroethylene ("CTFE") and hydrogen were supplied at flow rates of 500 Nml/min and 1800 Nml/min, respectively, from the starting material supply port of the reaction tube filled with the catalysts in the above manner and passed through the catalysts in the order of the upstream portion followed by the downstream portion. The temperature in the upstream portion was 320° C., and the temperature in the downstream portion was 230° C. In the above reaction, the contact time represented by W/Fo, i.e., the ratio of the catalyst amount in the reaction tube W (g) to the total flow rate of the fluoroethylene and hydrogen gas introduced into the reaction tube Fo, was 17 g·sec/cc.

Example 2

One 50 A reaction tube was prepared and filled with 670 g of catalysts. Each catalyst was formed using activated carbon as a carrier and using palladium as a noble metal. When the reaction tube was filled with the catalysts, a catalyst containing palladium in an amount of 0.3 mass % based on the total mass of the catalyst was formed as an upstream portion, and a catalyst containing palladium in an amount of 3 mass % based on the total mass of the catalyst was formed as a downstream portion. Chlorotrifluoroethylene ("CTFE") and hydrogen were supplied at flow rates of 500 Nml/min and 1800 Nml/min, respectively, from the starting material supply port of the reaction tube filled with the catalysts in the above manner and passed through the catalysts in the order of the upstream portion followed by the downstream portion. The temperature in the upstream portion was 250° C., and the temperature in the downstream portion was 160° C. In the above reaction, the contact time represented by W/Fo, i.e., the ratio of the catalyst amount in the reaction tube W (g) to the total flow rate of the fluoroethylene and hydrogen gas introduced into the reaction tube Fo, was 17 g·sec/cc.

Comparative Example 1

One 25-L reaction tube was prepared and filled with 810 g of a catalyst. The catalyst was formed using activated carbon as a carrier and using palladium as a noble metal. The amount of palladium supported was 0.6 mass % based on the total mass of the catalyst. CTFE and hydrogen were supplied at flow rates of 555 Nml/min and 1945 Nml/min, respectively, from the starting material supply port of the reaction tube; and passed through the catalyst. In the above reaction, the contact time represented by W/Fo, i.e., the ratio of the catalyst amount in the reaction tube W (g) to the total flow rate of the fluoroethylene and hydrogen gas introduced into the reaction tube Fo, was 19 g·sec/cc.

TABLE 1

|  | Detected amount (mol %) | |
| --- | --- | --- |
| Detected component | Example 1 | Example 2 |
| HFC-143 | 93.0 | 61.4 |
| HFO-1123 | 0.9 | 28.7 |
| HCFC-133b | 1.2 | 4.6 |
| HCFC-133 | 0.8 | 1.4 |
| CTFE | 0.0 | 0.0 |
| Reaction gas temperature (maximum temperature) | 438 | 335 |

Table 1 shows the results of gas chromatography in the Examples and Comparative Example.

Table 1 shows that in the hydrogenation reaction performed under the conditions in which the upstream portion and the downstream portion were provided in the reaction tube as in Example 1, the selectivity of the desired HFC-143 was high, and the amount of fluoroethylene (HFO-1123), which is an intermediate product, was low. Further, in Example 1, the introduction of other impurities was also suppressed, and no corrosion of the reaction tube or blockage due to a polymer was observed even after 400 hours of operation. In contrast, in Comparative Example 1, significant blockage of the reaction tube occurred during the reaction due to polymer formation. In Example 2, the reaction temperature was changed from that in Example 1, and the results show that HFC-143 and HFO-1123 contained in the product can be adjusted at any ratio. In Example 2 as well, no corrosion of the reaction tube or blockage due to a polymer was observed.

The invention claimed is:

1. A method for producing a product comprising a fluoroethane, wherein the fluoroethane is 1,1,2-trifluoroethane, the method comprising obtaining the product comprising the fluoroethane from a fluoroethylene comprising chlorotrifluoroethylene, wherein the fluoroethylene is represented by the following formula (3) by a reaction in the presence of catalysts:

$$CX^9F=CX^{10}X^{11} \quad (3),$$

wherein $X^9$, $X^{10}$, and $X^{11}$ are the same or different and each represents a hydrogen atom, a fluorine atom, or a chlorine atom, wherein each catalyst is formed by supporting a noble metal on a carrier;

a reactor for performing the reaction is filled with a catalyst having a noble metal concentration of C1 mass % based on the entire catalyst, and a catalyst having a noble metal concentration of C2 mass % based on the entire catalyst to form an upstream portion and a downstream portion, respectively, C1<C2, 0.01≤C1≤10, and 1≤C2≤15;

the reaction is performed by bringing the fluoroethylene represented by formula (3) and hydrogen gas into contact with the upstream portion and the downstream portion in this order, and the product comprising trifluoroethylene in an amount of 40 mol % or less based on the total amount of the product.

2. The method for producing a fluoroethane according to claim 1, wherein the noble metal is palladium.

3. The method according to claim 1, wherein the product comprises 1,1,2-trifluoroethane in an amount of 60 mol % or more based on the total amount of the product.

4. A method for producing a fluoroolefin, the method comprising:

conducting a reaction of a fluoroethylene represented by the following formula (3):

$$CX^9F=CX^{10}X^{11} \quad (3),$$

wherein $X^9$, $X^{10}$, and $X^{11}$ are the same or different and each represents a hydrogen atom, a fluorine atom, or a chlorine atom, in the presence of catalysts to obtain a product comprising a fluoroethane, wherein the fluoroethane is 1,1,2-trifluoroethane, wherein each catalyst is formed by supporting a noble metal on a carrier;

a reactor for performing the reaction is filled with a catalyst having a noble metal concentration of C1 mass % based on the entire catalyst, and a catalyst having a noble metal concentration of C2 mass % based on the entire catalyst to form an upstream portion and a downstream portion, respectively, C1<C2, 0.01≤C1≤10, and 1≤C2≤15;

the reaction is performed by bringing the fluoroethylene represented by formula (3) and hydrogen gas into contact with the upstream portion and the downstream portion in this order;

the fluoroethylene represented by formula (3) comprising chlorotrifluoroethylene, and the product comprising trifluoroethylene in an amount of 40 mol % or less based on the total amount of the product;

and conducting a dehydrofluorination reaction of the fluoroethane to obtain the fluoroolefin.

* * * * *